United States Patent
Harkrider, Jr.

[11] Patent Number: 6,146,397
[45] Date of Patent: Nov. 14, 2000

[54] ENDARTERECTOMY LOOP

[76] Inventor: William W. Harkrider, Jr., 602 N. Lewis St. Ste. 100, New Iberia, La. 70563

[21] Appl. No.: 09/286,653

[22] Filed: Apr. 6, 1999

[51] Int. Cl.[7] .................................................. A61B 17/22
[52] U.S. Cl. ............................................................. 606/159
[58] Field of Search .................................. 606/159, 170, 606/171, 110, 113

[56] References Cited

U.S. PATENT DOCUMENTS

| | | |
|---|---|---|
| D. 237,116 | 10/1975 | Ekbladh . |
| D. 282,965 | 3/1986 | Wellenstam . |
| D. 307,323 | 4/1990 | Scanlan . |
| 2,661,003 | 12/1953 | Devine et al. . |
| 2,779,334 | 1/1957 | Sandborn . |
| 2,868,206 | 1/1959 | Stoesser . |
| 3,185,155 | 5/1965 | Slaten et al. . |
| 3,568,677 | 3/1971 | Nolan et al. . |
| 3,741,214 | 6/1973 | Tillander . |
| 4,909,781 | 3/1990 | Husted ...................................... 606/194 |
| 5,013,310 | 5/1991 | Goode et al. . |
| 5,116,352 | 5/1992 | Schnepp-Pesch et al. . |
| 5,207,683 | 5/1993 | Goode et al. . |
| 5,387,219 | 2/1995 | Rappe . |
| 5,443,443 | 8/1995 | Shiber . |
| 5,498,249 | 3/1996 | Quinn ...................................... 604/280 |
| 5,522,819 | 6/1996 | Graves et al. . |
| 5,820,629 | 10/1998 | Cox . |
| 5,843,102 | 12/1998 | Kalmann et al. . |

*Primary Examiner*—Michael Buiz
*Assistant Examiner*—Vy Q. Bui
*Attorney, Agent, or Firm*—Rogers & Killeen

[57] ABSTRACT

An endarterectomy instrument and method for the treatment of alterosclerosis including a loop and a handle formed from a single strand of wire, the wire of the handle being twisted together to increase the rigidity thereof, but being sufficiently flexible to avoid perforation of the outer layer of the vessel. The angle and shape of the loop may be varied to fit the vessel. In some embodiments, the loop may be compressible to facilitate insertion through a small diameter lumen of a catheter.

19 Claims, 1 Drawing Sheet

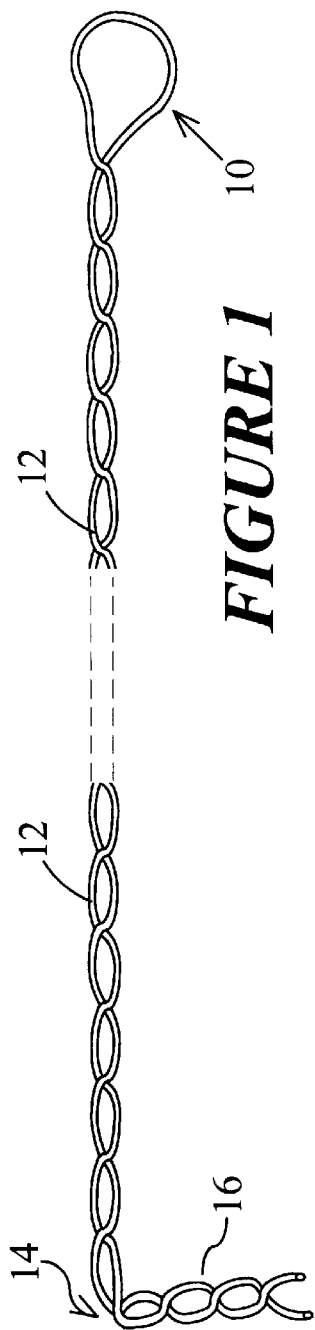
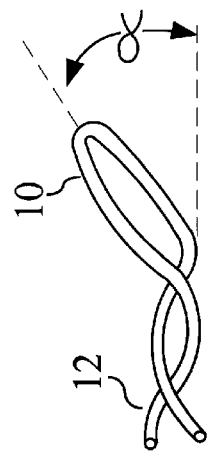
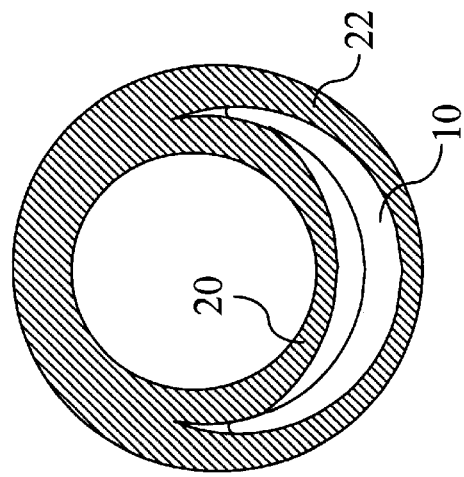
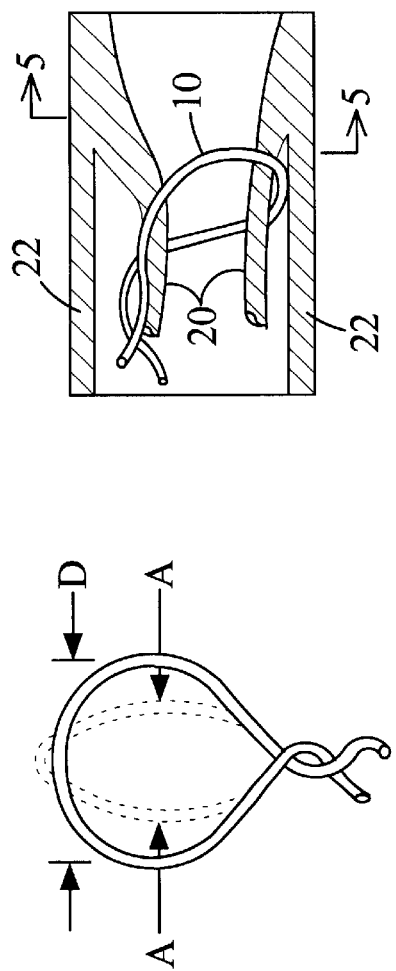
FIGURE 1
FIGURE 2
FIGURE 5
FIGURE 4
FIGURE 3

ENDARTERECTOMY LOOP

BACKGROUND OF THE INVENTION

This device relates to a device and method for the treatment of alterosclerosis, and more particularly to the removal of diseased tissue from an artery.

An artery is comprised of three layers including the outer layer or adventitia, a middle or smooth muscle layer, and an intima-tunica or intimal lining. Deposits collect on the intimal wall and result in stenosis, blockage or complete obstruction of the flow of blood through the artery. The procedure for removal of a diseased inner layer from within the adventitia is known as an endarterectomy, and a new and healthy intima will grow from the adventitia.

Devices for the removal of the intima are well known. Typically, an appropriately sized cylindrical ring with a blunt distal edge known as a ring stripper is inserted between the adventitia and intima and pushed along the artery to separate the intima from the outer wall of the vessel. At spaced intervals, an incision is made through the intima and the separated intima may then be withdrawn from the artery. An intima separation and cutting instrument is described in the Kalmann and Moll U.S. Pat. No. 5,843,102 dated Dec. 1, 1998 and a discussion thereof may be found in Ho et al, "The Mollring Cutter Remote Endarterectomy", J. Endovascular Surgery, 1995; 2:278–287.

Because the intima is generally separated from the outer wall by the presence of the ring stripper for some axial distance beyond the place where the intima is severed, a flap of the intima remains attached to the outer wall and may itself serve as an obstruction. It is further known to address this intima flap problem by vascular stents, but such stents are expensive and reduce the flexibility of the vessel. An alternative is described in the U.S. Pat. No. 5,820,629 dated Oct. 13, 1998 in which a smooth transition in the intimal lining is achieved by an electrocautery coil or a radially extending blade.

Instruments such as those described above are of course small, and tend to be very expensive and complicated to build. Sharp edges are potentially a problem because of the inherent risk of perforation of the outer wall of the artery. In addition, the diameter of the ring used to strip the intima from the outer wall of the artery is generally a constant and incapable of deformation to accommodate changes in the size of an artery for a specific patient or different patients. In addition, the rigidity of the ring and the elongated handle of commercially available ring strippers insures the ability to push the ring through the artery, but this rigidity also increases the risk, of perforation of the outer wall of the artery and makes it more difficult for the instrument to follow the artery through any deviations from a straight line.

It is accordingly an object of the present invention to provide a novel endarterectomy device and method which obviates many of the deficiencies of known devices and methods, which is simple in construction, readily modifiable in both size and shape to accommodate the wishes of the patient or the physician, easy to use, inexpensive, usable in either direction and constructed and configurable to assist dissection while preventing perforation of the outer wall of the artery. In some embodiments, the device may be insertable through a catheter significantly smaller than the artery.

These and many other objects and advantages of the present invention will be readily apparent to one skilled in the art to which the invention pertains from a perusal of the claims, the appended drawings, and the following detailed description of the preferred embodiments.

BRIEF DESCRIPTION OF THE DRAWINGS

FIG. 1 is a pictorial view of one embodiment of the endarterectomy device of the present invention.

FIG. 2 is an enlarged view of the distal end of the instrument of FIG. 1 illustrating the angle between the ring and the handle.

FIG. 3 is a an enlarged view of the distal end of the instrument of FIG. 1 illustrating changes in the shape thereof.

FIG. 4 is a side sectional view of the distal end of the instrument of FIG. 1 inserted within a blood vessel.

FIG. 5 is a cross-section taken through lines 5—5 of FIG. 4.

DESCRIPTION OF PREFERRED EMBODIMENTS

As illustrated in FIG. 1, one embodiment of the instrument of the present invention comprises a loop 10 at the distal end and a handle 12 extending from the loop 10 to the proximate end 14, where it may be bent at an angle of approximately 90° to form a radially extending extension 16. The extension 16 may be on any desired length and may be formed by the physician as needed during the procedure to facilitate the manual rotation of the loop 10 within the artery from the proximate end. The extension may also be preformed and covered with a suitable material such as a plastic to facilitate the gripping thereof by the physician to rotate the proximate end of the handle. The use of a plastic covering for the extension also facilitates the marking of the instrument, e.g., to indicate the size of the loop and/or the stiffness of the handle.

As shown in FIG. 2, the loop 10 is desirably formed at an angle α to the handle 12. However, it has been found convenient to manufacture the device without any angle and to encourage the physician performing the procedure to manually vary the angle α to accommodate the circumstances he finds. Assuming a generally circular cross-section of the loop 10, making the angle smaller will of course make the effective cross-section of the loop 10 elliptical and permit the use of the instrument in smaller arteries. Increasing the angle will result in a greater tendency of the handle of the instrument to bend when the loop 10 encounters an obstruction within the artery and reduce the physician's ability to push the loop 10 through the artery. While the angle may vary from 0° to 90°, it has been found in practice that an angle between about 15° and about 65° is generally effective, preferably between about 30° and 60°.

The diameter of the loop 10 may be made to vary to fit the size of the vessel in which it is to be inserted. It has been found convenient to have a diameter between about 1 mm and about 10 mm, possibly 12 mm, but diameters between about 3 mm and 8 mm are generally effective.

As shown in FIG. 3, the shape of the loop 10 may also be manually varied by the physician. The application of pressure between the thumb and forefinger of the physician to the sides of the loop 10 at points A will reduce the diameter D of the loop and increase its length. The resiliency of the material of the loop will determine how much deformation is required to effect a permanent as contrasted with resilient change in the shape of the loop.

The loop 10 and handle 12 are desirably made of a single strand of metal wire, preferably stainless steel or some other material inert to the tissue of the patient to thereby reduce the possibility of any reaction with the patient. However, the loop 10 and handle 12 may be made of different materials and may be secured together in any suitable conventional manner. For example, the handle may be made of a flat metal ribbon or suitable plastic with the desired flexibility and other characteristics.

It is desirable that at least the loop, and preferably the handle, be opaque to x-rays and fluoroscopy so that the position of the instrument within the artery may be viewed by conventional operating room equipment.

In the preferred embodiment of FIG. 1, the loop and handle are made from a single wire with the loop formed in the center over a suitable mandrel and the two ends twisted together to form the elongated handle. The twisted strands increase the rigidity of the handle over a single strand, and yet do not destroy the flexibility needed to insure that the loop is not pushed through the outer wall of the artery, i.e., resistance against axial movement of the loop through the artery will cause the handle to flex within the artery. In the preferred embodiment, the rate of twist is between about 3 and about 12 twists per inch of length, preferably between about 5 and about 7 twists per inch of length.

Where the wire of the handle is twisted, it has been found convenient to coat the handle with a suitable inert plastic to avoid the inadvertent entanglement of the handle with the artery, e.g., where the artery bends or the handle flexes in response to resistance encountered by the loop.

The wire is desirably between about 0.15 mm or 0.007 inches in diameter to about 1.22 mm or 0.048 inches in diameter, preferably between about 0.50 mm and about 0.80 mm in diameter.

In operation, access may be obtained to the blood vessel in the conventional manner by incision and the loop at the distal end of the instrument inserted into the artery. By the proper selection of loop size and shape, the loop can be made to conform generally to the inner diameter of the outer wall of the vessel, so that passage of the loop down the vessel will separate the intima from the outer wall and force it toward the center of the vessel. The circular cross-section of the wire provides a blunt curved leading edge which is desirable to avoid penetration of the outer wall and the premature cutting of the intima from the outer wall. As shown in FIG. 4 and FIG. 5, the angle a of the loop 10 to the handle facilitates the separation of the intima 20 from the outer wall 22 of the vessel.

Once the desired passage has been completed, the physician may rotate the loop 10 at the distal end of the instrument by rotating the handle 12 at the proximate end 14. As shown in FIG. 1, the handle may be bent by the physician to facilitate rotation. Rotation of the loop 10 will effect separation of the intima 20 from the outer wall 22 and will engage the separated intima sufficiently to permit the withdrawal of the separated intima from the vessel by the withdrawal of the instrument.

The instrument of the present invention may also be inserted, like any other instrument, into the patient through a lumen in a catheter such as disclosed and claimed in applicant's copending U.S. patent application Ser. No. 09/276,679 filed Mar. 26, 1999 for "ENDOLUMINAL MULTI-LUMINAL SURGICAL SHEATH AND METHOD",the content of which is hereby incorporated herein by reference.

The flexibility of the loop 10 provides another advantage when the instrument is used with a catheter in that the lumen of the catheter will be smaller in diameter than the vessel. The flexibility of the loop permits resilient radial compression so long as the loop remains within the catheter, and radial expansion to the size of the vessel once the loop is no longer confined by the catheter. The use of the instrument with a catheter permits the use of optics with the instrument and the use of other suitable conventional instruments to address any residual tissue problems associated with the separation of the intima from the outer wall by rotation of the loop.

While preferred embodiments of the present invention have been described, it is to be understood that the embodiments described are illustrative only and the scope of the invention is to be defined solely by the appended claims when accorded a full range of equivalence, many variations and modifications naturally occurring to those of skill in the art from a perusal hereof.

What is claimed is:

1. An instrument for treating a blood vessel comprising:
   a single strand of solid material generally circular in cross-section, said material being formed into a single generally circular loop sufficiently flexible for insertion into a blood vessel to separate the intima from the outer layer of the vessel; and
   an elongated handle attached at the distal end to said wire loop at a predetermined angle less than 90°,
      said handle being sufficiently rigid to push said loop along the interior of the vessel to effect separation of the intima and any associated plaque from the outer layer of the vessel and being sufficiently flexible to bend when said loop encounters resistance to passage through the vessel to thereby reduce the likelihood of perforation of the outer layer of the vessel.

2. The instrument of claim 1 wherein said handle is formed from single strand of solid material generally circular in cross-section and integral with said wire loop.

3. The instrument of claim 2 wherein said handle and said loop are formed from the same material.

4. The instrument of claim 1 wherein said handle comprises twisted strands of a solid material of generally circular cross-section to thereby increase the rigidity of the handle.

5. The instrument of claim 4 wherein the handle is covered by an inert material to reduce the likelihood of inadvertent entanglement of the handle with the vessel.

6. The instrument of claim 1 wherein said loop is opaque to x-rays.

7. The instrument of claim 6 wherein said loop is a metal wire.

8. The instrument of claim 1 wherein said handle comprises twisted strands of a solid material of generally circular cross-section to thereby increase the rigidity of the handle.

9. The instrument of claim 8 wherein said handle and said loop are formed from the same metal wire.

10. The instrument of claim 1 wherein a small portion at the proximate end of said handle is bent at an angle of about 90° with respect to the length of the handle.

11. The instrument of claim 10 wherein said small portion is covered by an inert material with identifying indicia.

12. The instrument of claim 1 wherein said loop is deformable in shape.

13. The instrument of claim 12 wherein the characteristics of the material of said loop are such that said loop may be permanently deformed under the pressure from the fingers of a physician.

14. The instrument of claim 12 wherein the characteristics of the material of said loop are such that said loop may be resiliently deformed under the pressure from the lumen of a catheter smaller in diameter than the diameter of said undeformed loop.

15. The instrument of claim 12 wherein the angle of attachment of said loop to said handle is variable under the pressure from the fingers of a physician.

16. The instrument of claim 1 where angle of attachment is of said loop to said handle is variable under the pressure from the fingers of a physician.

17. The instrument of claim 1 wherein said loop is sufficiently flexible to be laterally compressed by insertion through a lumen in a catheter into a blood vessel which is about ten percent larger in diameter than the lumen and expandable once the loop exits the distal end of the lumen to the size of the blood vessel.

18. A method of removing the intima and any associated plaque from a blood vessel comprising the steps of:

(a) making an incision in a blood vessel;

(b) inserting a single loop formed from a single strand of material of generally circular cross-section into the vessel, and selectively varying the orientation of the loop relative to the axis of the vessel to position the loop between the intima and the outer wall of the blood vessel;

(c) moving the loop through the vessel to thereby separate the intima and associated plaque from the outer wall without using a cutting edge;

(d) rotating the loop to sever the separated intima and any associated plaque from the intima attached to the outer wall;

(d) withdrawing the loop and the separated intima for the vessel through the incision.

19. A method of removing the intima and associated plaque from a blood vessel comprising the steps of:

(a) making an incision in a blood vessel;

(b) inserting a multilumen catheter into the incision;

(c) inserting a single compressible loop formed from a single strand of material of generally circular cross-section through a lumen of the catheter into the vessel to position the loop between the intima and the outer wall of the blood vessel, the diameter of the uncompressed loop being about ten percent greater than the diameter of the lumen through which inserted;

(d) moving the loop through the vessel to thereby separate the intima and any associated plaque from the outer wall over the distance through which moved without using a cutting edge;

(e) rotating the loop to sever the separated intima and associated plaque from the intima attached to the outer wall;

(f) withdrawing the loop and the separated intima and associated plaque for the vessel through the lumen of the catheter.

* * * * *